US00PP14939P2

(12) United States Plant Patent
Noodelijk

(10) Patent No.: US PP14,939 P2
(45) Date of Patent: Jun. 22, 2004

(54) CHRYSANTHEMUM PLANT NAMED 'CEFREYA'

(50) Latin Name: *Chrysanthemum morifolium*
Varietal Denomination: Cefreya

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 30 days.

(21) Appl. No.: 10/316,870

(22) Filed: Dec. 12, 2002

(51) Int. Cl.[7] ..... A01H 5/00
(52) U.S. Cl. ..... Plt./297

(58) Field of Search ..... Plt./297

(56) References Cited

PUBLICATIONS

UPOV–ROM Plant Variety Database, hit on 'Freya', 2003/03.*

* cited by examiner

*Primary Examiner*—Anne Marie Grunberg
(74) *Attorney, Agent, or Firm*—Parkhurst & Wendel, L.L.P.

(57) ABSTRACT

A chrysanthemum plant named 'Cefreya' characterized by its medium sized blooms with coral-salmon ray florets and prolific branching, natural season flower date September 1–5; blooming for a period of 5 weeks.

3 Drawing Sheets

BACKGROUND OF THE INVENTION

'Cefreya' is a product of a breeding and selection program for outdoor pot mums (garden mums) that had the objective of creating new chrysanthemum cultivars with a decorative type flower, a natural season flower date around September 1–5, and a blooming for a period of 5 weeks. The new plant of the present invention comprises a new and distinct cultivar of Chrysanthemum plant 'Cefreya', which is a seedling resulting from the open pollination among groups of chrysanthemum cultivars maintained under the control of the inventor for breeding purposes. The identity of the parent plants yielding this new chrysanthemum plant is unknown. The new and distinct cultivar was discovered and selected as one flowering plant by Rob Noodelijk on a cultivated field in Rijsenhout, Holland in September 2000. The plant has been asexually reproduced by cuttings in greenhouses at Rijsenhout, Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
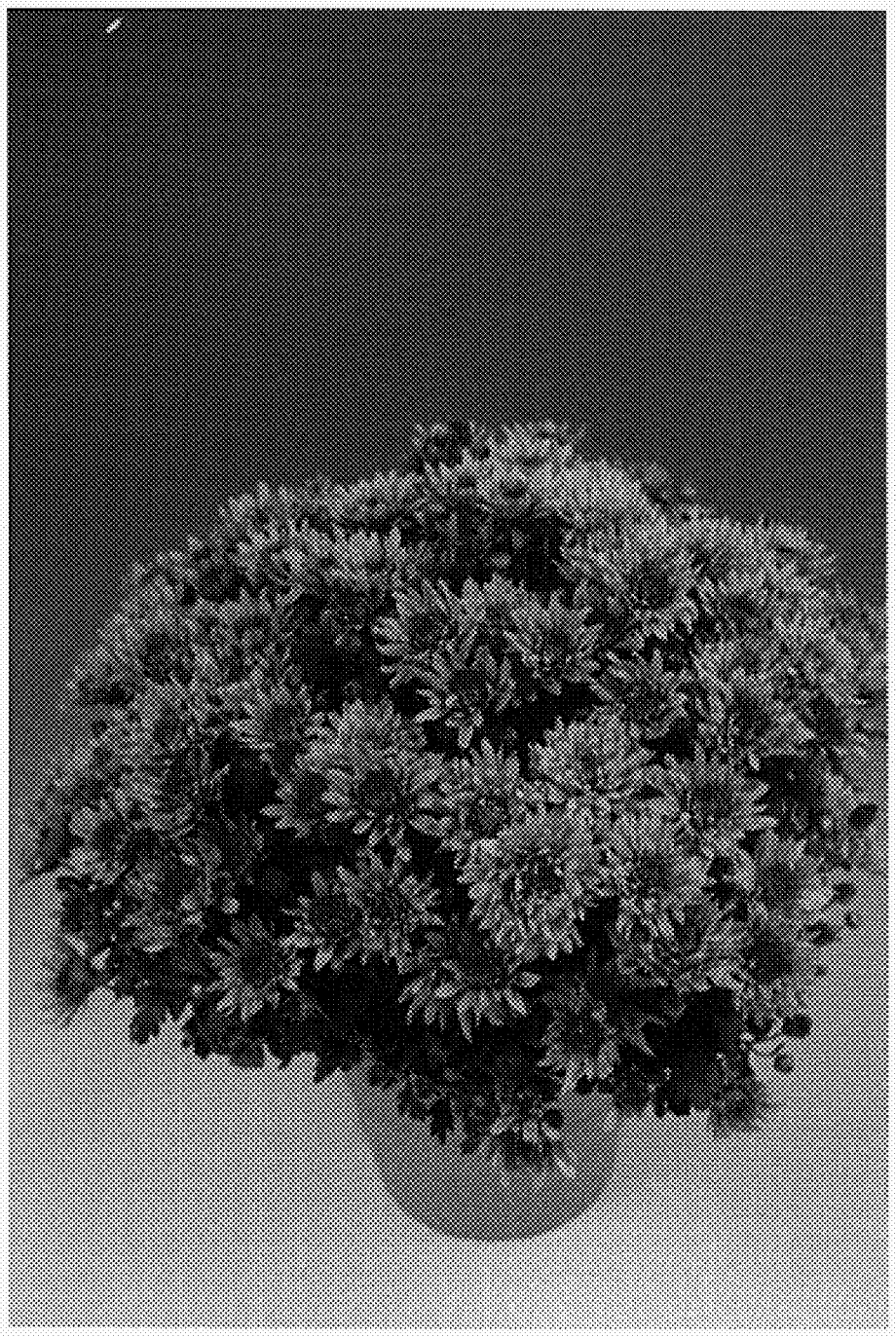
FIG. 1 shows a plant of the cultivar in full bloom.
Figure 2:
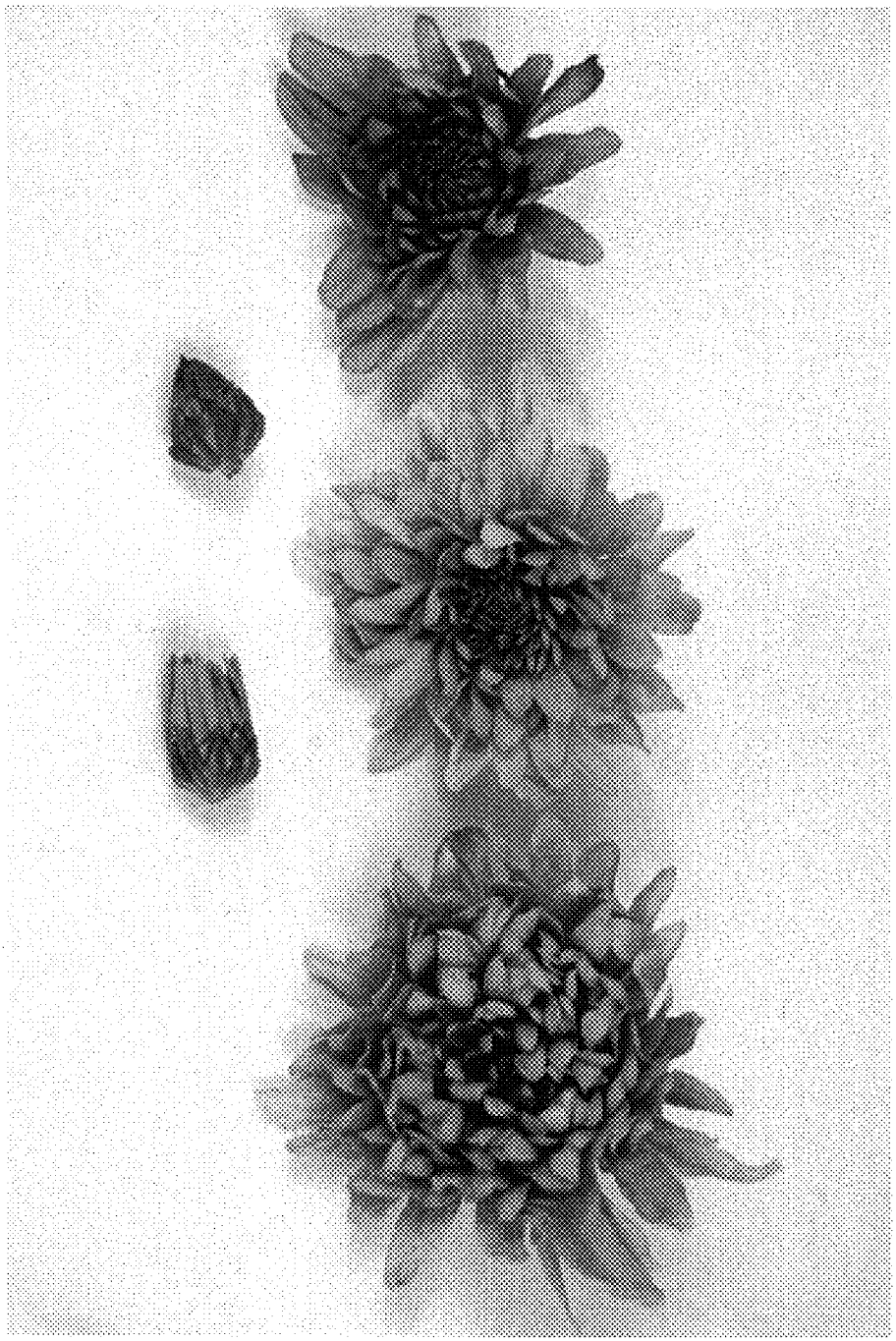
FIG. 2 shows the various stages of bloom of the new cultivar.
Figure 3:
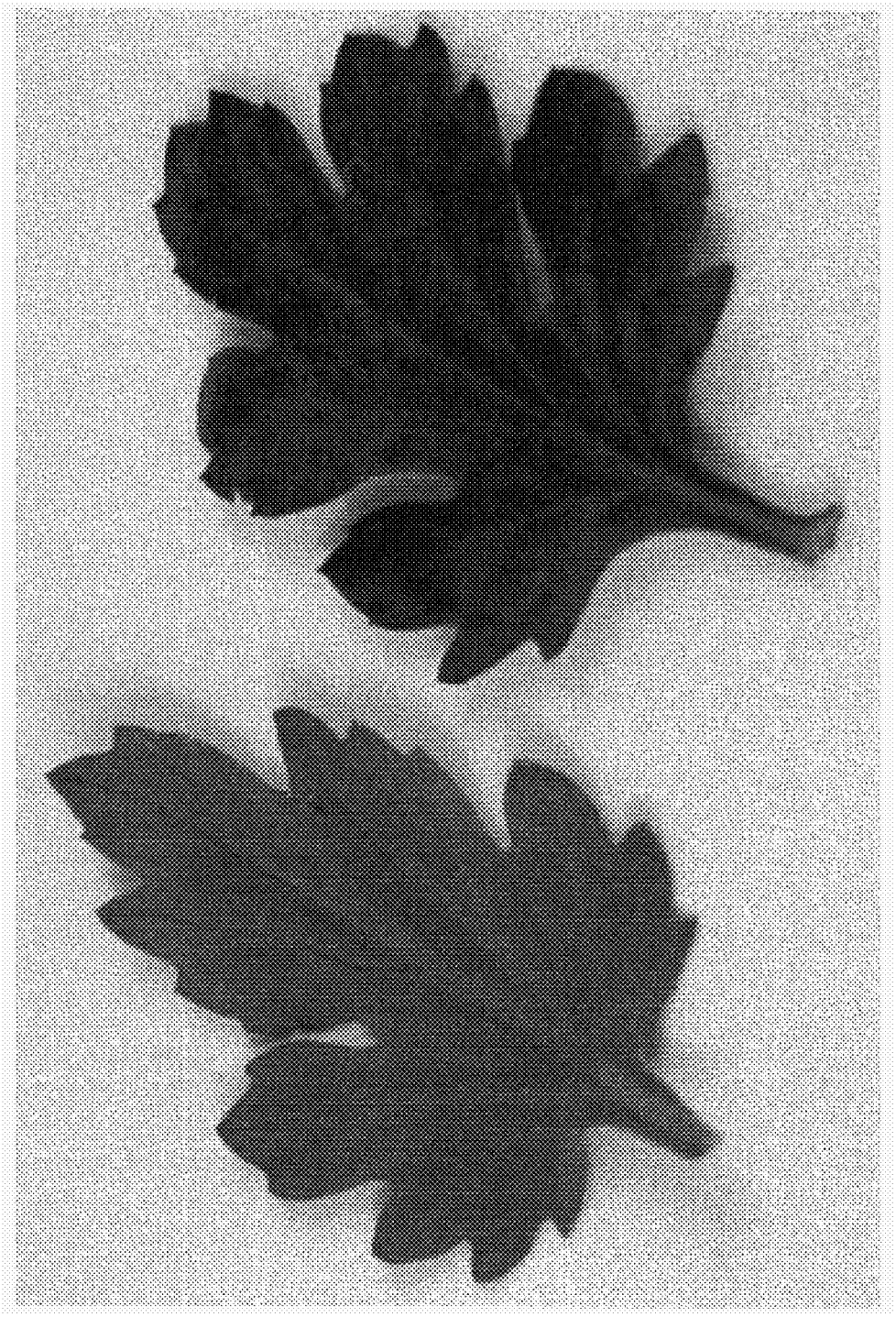
FIG. 3 shows the petiole and foliage of the new cultivar.

This new variety of chrysanthemum is of the botanical classification *Chrysanthemum morifolium*. The observations and measurements were gathered from plants grown out door in Rijsenhout, Holland under natural day length and temperature and planted week 22 in 2000 and 2001. The natural blooming date of this crop was September 1–5 (week 35). The average height of the plants was 27 cms. No growth retardants were used. No tests were done on disease or insect resistance or susceptibility. No tests were done on cold or drought tolerance. This new variety produces medium sized blooms with coral-salmon ray florets and a red center blooming for a period of 5 weeks.

From the cultivars known to inventor the most similar existing cultivar in comparison to 'Cefreya' is 'Grenadine' (U.S. Plant Pat. No. 5,338). When 'Grenadine' and 'Cefreya' are being compared the following differences are noticed: The differences of 'Grenadine' and 'Cefreya' are (1) Flower form. Both 'Cefreya' and 'Grenadine' have a coral-salmon decorative flower; however the ray-florets differ in form. (2) Natural flowering date. 'Cefreya' flowers earlier.

The following is a description of the plant and characteristics that distinguish 'Cefreya' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, 1995 edition.

Table 1. Botanical Description of Cultivar 'Cefreya'

Bud:
- *Size*.—Medium; cross-section 1.0 cm, height 1.5 cm.
- *Outside color*.—Red 37B.
- *Involucral bracts*.—2 rows, length 7 mm, width 3 mm.
- *Involucral bracts among disc-florets*.—Not present.
- *Involucral bracts color*.—Green 138B.

Bloom:
- *Type*.—Decorative.
- *Height*.—High; 2.5 cm.
- *Size*.—Medium.
- *Fully expanded*.—5.5–6.0 cm.
- *Number of blooms per branch*.—Approx. 4–6 blooms per branch.

*Performance on the plant*.—5 weeks.
*Seeds* (*if crossed*).—Produced in small quantities, ovate grey-brown 199A, 1½ mm in length.
*Fragrance*.—Typical chrysanthemum, slightly.

Color:
*Center of the flower*.—Immature red 37A. Mature red 37C.
*Color of upper surface of the ray-florets*.—Red 37B.
*Color of the lower surface of the ray-florets*.—Red 37C.
*Tonality from distance*.—A garden mum with coral-salmon flowers and a red disc.
*Color of the upper surface of the ray-florets after aging of the plant*.—Red 37C.

Ray florets:
*Texture*.—Upper and under side smooth.
*Number*.—140–150.
*Cross-section*.—Flat.
*Longitudinal axis of majority*.—Reflexing to twisted.
*Length of corolla tube*.—Short 0.3 cm.
*Ray-floret margin*.—Entire.
*Ray-floret length*.—2.6–2.8 cm.
*Ray-floret width*.—0.6 cm.
*Ratio length/width*.—High.
*Shape of tip*.—Rounded.
*Disc florets*.—None.
*Receptacle shape*.—Conical raised.

Reproductive organs:
*Stamen*.—Absent.
*Pollen*.—None.
*Styles*.—Thin.
*Style color*.—Yellow-green 144A.
*Style length*.—4 mm.
*Stigmas*.—Yellow-green 144A.
*Stigma width*.—1 mm.
*Ovaries*.—Enclosed in calyx.

Plant:
*Form*.—Grown as spray-type pot mum, outdoor mounded and round.
*Growth habit*.—Spreading.
*Growth rate*.—Moderate.
*Height*.—27 cm.
*Width*.—32–34 cm.
*Stem color*.—Green 139B.
*Stem strength*.—Strong.
*Stem brittleness*.—Present.
*Stem anthocyanin coloration*.—Absent.
*Length of lateral branch*.—From top to bottom 13–14 cm.
*Lateral branch color*.—Green 139B.
*Lateral branch, attachment*.—Flexible.
*Branching* (*average number of lateral branches*).—Prolific with 7–8 breaks after pinching.
*Peduncle length*.—6.0 cm.
*Peduncle color*.—Green 139B.
*Natural season blooming date*.—September 1–5.

Foliage:
*Color*.—Upper side green 139A. Under side green 139C.
*Size*.—Medium; length 5.0 cm, width 4.0 cm.
*Quantity* (*number per lateral branch*).—8–9.
*Shape*.—Ovate.
*Texture upper side*.—Glabrous.
*Texture under side*.—Pubescent.
*Venation arrangement*.—Palmate.
*Shape of the margin*.—Serrated.
*Shape of base of sinus between lateral lobes*.—Round.
*Margin of sinus between lateral lobes*.—Converging.
*Shape of base*.—Truncate.
*Apex*.—Cuspidate.

TABLE 2

Differences with the comparison varieties

| | 'Cefreya' | 'GRENADINE' |
|---|---|---|
| Longitudinal axis of ray-florets | Reflexing to twisted | Incurved |
| Cross section of ray-florets | Flat | Concave |
| Natural flowering date | September 1–5 | September 17–25 |

I claim:

1. A new and distinct variety of chrysanthemum plant as described and illustrated.

* * * * *